US010428384B2

(12) United States Patent
Redei

(10) Patent No.: US 10,428,384 B2
(45) Date of Patent: Oct. 1, 2019

(54) BIOMARKERS FOR POST-TRAUMATIC STRESS STATES

(71) Applicant: Northwestern University, Evanston, IL (US)

(72) Inventor: Eva E. Redei, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/913,511

(22) Filed: Mar. 6, 2018

(65) Prior Publication Data

US 2019/0048419 A1  Feb. 14, 2019

Related U.S. Application Data

(63) Continuation of application No. 14/569,127, filed on Dec. 12, 2014, now Pat. No. 9,909,181.

(60) Provisional application No. 61/915,861, filed on Dec. 13, 2013.

(51) Int. Cl.
*C12Q 1/6883* (2018.01)

(52) U.S. Cl.
CPC ..... *C12Q 1/6883* (2013.01); *C12Q 2600/158* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis et al. |
| 4,800,159 A | 1/1989 | Mullis et al. |
| 4,965,188 A | 10/1990 | Mullis et al. |
| 5,011,769 A | 4/1991 | Duck et al. |
| 5,124,246 A | 6/1992 | Urdea et al. |
| 5,130,238 A | 7/1992 | Malek et al. |
| 5,270,184 A | 12/1993 | Walker et al. |
| 5,283,174 A | 2/1994 | Arnold, Jr. et al. |
| 5,288,609 A | 2/1994 | Engelhardt et al. |
| 5,399,491 A | 3/1995 | Kacian et al. |
| 5,403,711 A | 4/1995 | Walder et al. |
| 5,409,818 A | 4/1995 | Davey et al. |
| 5,455,166 A | 10/1995 | Walker |
| 5,538,848 A | 7/1996 | Livak et al. |
| 5,624,802 A | 4/1997 | Urdea et al. |
| 5,660,988 A | 8/1997 | Duck et al. |
| 5,710,029 A | 1/1998 | Ryder et al. |
| 5,710,264 A | 1/1998 | Urdea et al. |
| 5,750,341 A | 5/1998 | Macevicz |
| 5,792,614 A | 8/1998 | Western et al. |
| 5,814,447 A | 9/1998 | Ishiguro et al. |
| 5,824,518 A | 10/1998 | Kacian et al. |
| 5,846,717 A | 12/1998 | Brow et al. |
| 5,849,481 A | 12/1998 | Urdea et al. |
| 5,851,770 A | 12/1998 | Babon et al. |
| 5,882,867 A | 3/1999 | Ullman et al. |
| 5,914,230 A | 6/1999 | Liu et al. |
| 5,925,517 A | 7/1999 | Tyagi et al. |
| 5,928,862 A | 7/1999 | Morrison |
| 5,958,692 A | 9/1999 | Cotton et al. |
| 5,985,557 A | 11/1999 | Prudent et al. |
| 5,994,069 A | 11/1999 | Hall et al. |
| 6,001,567 A | 12/1999 | Brow et al. |
| 6,013,170 A | 1/2000 | Meade |
| 6,063,573 A | 5/2000 | Kayyem |
| 6,090,543 A | 7/2000 | Prudent et al. |
| 6,110,677 A | 8/2000 | Western et al. |
| 6,110,684 A | 8/2000 | Kemper et al. |
| 6,121,001 A | 9/2000 | Western et al. |
| 6,150,097 A | 11/2000 | Tyagi et al. |
| 6,183,960 B1 | 2/2001 | Lizardi |
| 6,210,884 B1 | 4/2001 | Lizardi |
| 6,221,583 B1 | 4/2001 | Kayyem et al. |
| 6,235,502 B1 | 5/2001 | Weissman et al. |
| 6,248,229 B1 | 6/2001 | Meade |
| 6,303,305 B1 | 10/2001 | Wittwer et al. |
| 6,306,597 B1 | 10/2001 | Macevicz |
| 6,485,944 B1 | 11/2002 | Church et al. |
| 6,511,803 B1 | 1/2003 | Church et al. |
| 6,534,274 B2 | 3/2003 | Becker et al. |
| 6,541,205 B1 | 4/2003 | Yokoyama et al. |
| 6,787,308 B2 | 9/2004 | Balasubramanian et al. |
| 6,833,246 B2 | 12/2004 | Balasubramanian |
| 7,323,305 B2 | 1/2008 | Leamon et al. |

(Continued)

FOREIGN PATENT DOCUMENTS

| | | |
|---|---|---|
| EP | 0265244 | 9/1992 |
| WO | WO 00/018957 | 4/2000 |

(Continued)

OTHER PUBLICATIONS

The Mammalian Gene Collection (https://genecollections.nci.nih.gov/MGC/ last updated Mar. 2009 and accessed online May 15, 2019.*

(Continued)

*Primary Examiner* — Amanda Haney
(74) *Attorney, Agent, or Firm* — Casimir Jones SC; David W. Staple

(57) ABSTRACT

The present invention relates generally to the detection or diagnosis of post-traumatic stress states in a subject, and provides methods, reagents, and kits useful for this purpose. Provided herein are biomarkers that are indicative of and/or diagnostic of post-traumatic stress states including PTSD.

20 Claims, No Drawings

(56) References Cited

U.S. PATENT DOCUMENTS

| | | |
|---|---|---|
| 7,374,885 B2 | 5/2008 | Becker et al. |
| 8,679,789 B2 | 3/2014 | Arnold et al. |
| 9,909,181 B2 | 3/2018 | Redei |
| 2005/0042638 A1 | 2/2005 | Arnold et al. |
| 2006/0046265 A1 | 3/2006 | Becker et al. |
| 2010/0248230 A1 | 9/2010 | Schlaak et al. |
| 2011/0046006 A1 | 2/2011 | Spijker et al. |
| 2012/0077702 A1 | 3/2012 | Love et al. |
| 2012/0094859 A1 | 4/2012 | Redei et al. |
| 2013/0237454 A1 | 9/2013 | Schutzer et al. |
| 2014/0073516 A1 | 3/2014 | Hood et al. |

FOREIGN PATENT DOCUMENTS

| | | |
|---|---|---|
| WO | WO 2006084132 | 8/2006 |
| WO | WO 2013020057 | 2/2013 |
| WO | WO 2015089438 | 6/2015 |

OTHER PUBLICATIONS

Adessi et al., Solid phase DNA amplification: characterisation of primer attachment and amplification mechanisms, Nucleic Acid Res. 2010; 28:E87.

Andrus et al., Gene expression patterns in the hippocampus and amygdala of endogenous depression and chronic stress models. Molecular psychiatry 2012; 17: 49-61.

Barnay, Genetic disease detection and DNA amplification using cloned thermostable ligase, Proc. Natl. Acad. Sci USA 1991; 88:189-93.

Bennett et al., Toward the 1,000 dollars human genome, 2005, Pharmacogenomics. Jun. 2005;6(4):373-8.

Birren et al., Genome Analysis: Analyzing DNA, 1, Cold Spring Harbor, N.Y.

Brenner et al., Gene expression analysis by massively parallel signature sequencing (MPSS) on microbead arrays, Nat Biotechnol. Jun. 2000;18(6):630-4.

Chinnaiyan et al., Mechanisms of enhanced radiation response following epidermal growth factor receptor signaling inhibition by erlotinib (Tarceva), Cancer Res 2005; 65:3328-35.

Feodorova et al., Psychological stress—cellular and molecular mechanisms. Folia Med (Plovdiv). Jul.-Sep. 2012;54(3):5-13.

Glatt et al., Blood-based gene-expression predictors of PTSD risk and resilience among deployed marines: a pilot study. Am J Med Genet B Neuropsychiatr Genet. Jun. 2013;162B(4):313-26.

Guatelli et al., Isothermal, in vitro amplification of nucleic acids by a multienzyme reaction modeled after retroviral replication, Proc. Natl. Acad. Sci. USA 1990; 87: 1874-1878.

Kwoh et al., Transcription-based amplification system and detection of amplified human immunodeficiency virus type 1 with a bead-based sandwich hybridization format, Proc. Natl. Acad. Sci. USA1989; 86:1173-1177.

Lizardi et al., Exponential Amplification of Recombinant- RNA Hybridization Probes, Nature BioTechnol. 1988; 6: 1197-1202.

Maclean et al., Application of 'next-generation' sequencing technologies to microbial genetics, Nature Rev. Microbiol. 2009, 7: 287-296.

The Mammalian Gene Collection. Retrieved from: https://genecollections.nci.nih.gov/MGC/, last updated Mar. 2009, retrieved May 1, 2017, 2 pages.

Margulies et al., Genome sequencing in microfabricated high-density picolitre reactors, Nature. 2005; 437(7057):376-80.

Mitra et al., Fluorescent in situ sequencing on polymerase colonies, 2003, Anal Biochem. Sep. 1, 2003;320(1):55-65.

Mullis et al., Specific synthesis of DNA in vitro via a polymerase-catalyzed chain reaction., Methods Enzymol. 1987;155:335-50.

Murakawa et al., Direct detection of HIV-1 RNA from AIDS and ARC patient samples, DNA. May 1988;7(4):287-9.

Nelson et al., Detection of Acridinium Esters by Chemiluminescence, Nonisotopic Probing, Blotting, and Sequencing, ch. 17, Larry J. Kricka ed., 2d ed., 1995, pp. 391-428.

Persing, "In Vitro Nucleic Acid Amplification Techniques" in Diagnostic Medical Microbiology: Principles and Applications (Persing et al., Eds.), pp. 51-87 (American Society for Microbiology, Washington, DC (1993).

Rubin et al., Overexpression, amplification, and androgen regulation of TPD52 in prostate cancer, Cancer Res. 2004;64(11):3814-22.

Segman et al., Peripheral blood mononuclear cell gene expression profiles identify emergent post-traumatic stress disorder among trauma survivors, Molecular Psychiatry 2005; 10:500-513.

Shendure et al., Accurate multiplex polony sequencing of an evolved bacterial genome, Science. 2005; 309(5741):1728-32.

Voelkerding et al., Next-generation sequencing: from basic research to diagnostics, Clin Chem. Apr. 2009;55(4):641-58.

Vogelstein et al., Digital PCR, Proc Natl Acad Sci U S A. Aug. 3, 1999;96(16):9236-4.

Walker et al., Isothermal in vitro amplification of DNA by a restriction enzyme/DNA polymerase system, Proc Natl Acad Sci U S A. Jan. 1, 1992;89(1):392-6.

Weiss, Hot prospect for new gene amplifier, Science. Nov. 29, 1991;254(5036):1292-3.

International Search Report and Written Opinion for PCT/US2014/070088, dated May 20, 2015, 12 pages.

\* cited by examiner

BIOMARKERS FOR POST-TRAUMATIC STRESS STATES

The present application is a continuation of U.S. patent application Ser. No. 14/569,127, filed Dec. 12, 2014, now allowed, which claims priority to U.S. Provisional Patent Application Ser. No. 61/915,861, filed Dec. 13, 2013, the disclosure of which is herein incorporated by reference in its entirety.

STATEMENT REGARDING FEDERAL FUNDING

This invention was made with government support under R21 MH077234 awarded by the National Institutes of Health. The government has certain rights in the invention.

FIELD

The present invention relates generally to the detection or diagnosis of post-traumatic stress states in a subject, and provides methods, reagents, and kits useful for this purpose. Provided herein are biomarkers that are indicative of and/or diagnostic of post-traumatic stress states including PTSD.

BACKGROUND

Approximately 6.8% of persons in the United States develop post-traumatic stress states, or as it is most commonly known PTSD, at some time in their lives. Experiences that most often give rise to PTSD include rape, assault, and combat; natural disasters or man-made accidents. More than 20 percent of the troops who fought in the Iraq and Afghanistan wars may be diagnosed with PTSD. PTSD is a condition that occurs following exposure to an extremely traumatic experience that results in an intense and prolonged response to stress. Most individuals who experience a traumatic event at some time during their lives will recover. A subset of individuals, however, develop PTSD. Biomarkers that diagnose and approximate PTSD risk would be of great value. Biomarker discovery in PTSD has been hindered by the lack of prospective studies in traumatized individuals.

SUMMARY

The present invention relates generally to the detection or diagnosis of post-traumatic stress states in a subject, and provides methods, reagents, and kits useful for this purpose. Provided herein are biomarkers that are indicative of and/or diagnostic of post-traumatic stress states including PTSD.

In some embodiments, the present invention provides methods for characterizing a subject as suffering from post-traumatic stress disorder, comprising: (a) detecting, in a sample obtained from the subject, the levels of expression products of a panel of multiple biomarkers selected from the genes listed in Table 1 (e.g., using reagents and analytical techniques described herein); and (b) characterizing the risk of post-traumatic stress disorders in the subject based on the levels of the expression products. In some embodiments, a subject is diagnosed as having a post-traumatic stress disorder. In some embodiments, methods further comprise taking one or more intervention steps to treat or prevent the post-traumatic stress disorder. In some embodiments, methods further comprise subsequent re-testing for biomakers of post-traumatic stress disorder (e.g., after treatment, after a particular time period (e.g., 1 week, 1 month, 6 months, 1 year, 2 years, etc.). In some embodiments, the subject is a human subject. In some embodiments, the sample is a tissue or fluid (e.g., urine, blood, saliva, etc.) sample. In some embodiments, the sample is a blood sample (e.g., whole blood, plasma, processed blood, etc.). In some embodiments, the human subject is suspected of suffering from PTSD based on the presence of symptoms of PTSD, a prior traumatic event or series of events, or a combination thereof.

In some embodiments, the panel of biomarkers comprises one or more (e.g., 1, 2, 3) of SERPINB1, LILRB3, and GLRX. In some embodiments, the panel of biomarkers comprises one or more (e.g., 1, 2, 3, 4, 5, 6, 7, 8, 9, 10, 11) of IFI27, FUOM, HSPA8, IGK, LCMT1, THYN1, SEC14L2, SLC16A3, SERINC2, TRPM6, and XKRX. In some embodiments, the panel further comprises one or more of CYP21A1, ADN, DGAT2, PROK2, TNFRSF1A and ELOVL5. In some embodiments, the panel of biomarkers comprises one or more of IFI27, FUOM, HSPA8, IGK, LCMT1, THYN1, SEC14L2, SLC16A3, SERINC2, TRPM6, XKRX, CYP21A1, ADN, DGAT2, PROK2, TNFRSF1A and ELOVL5. In some embodiments, the panel of PTSD biomarkers comprises or consists of 100 or fewer PTSD biomarkers (e.g., <100 biomarkers, <50 biomarkers, <40 biomarkers, <30 biomarkers, <20 biomarkers, <10 biomarkers). In some embodiments, the panel of PTSD biomarkers comprises or consists of two of more PTSD biomarkers (e.g., >3 biomarkers, >4 biomarkers, >5 biomarkers, >6 biomarkers, >7 biomarkers, >8 biomarkers, >9 biomarkers, >10 biomarkers, >15 biomarkers, >20 biomarkers, >30 biomarkers, >40 biomarkers). In some embodiments, the PTSD panel is part of a larger panel of biomarkers (e.g., a panel that also screens for other diseases or conditions). In some embodiments, the PTSD panel is part of a larger general panel of biomarkers, wherein the general panel comprises or consists of 10,000 or fewer biomarkers (e.g., <5,000 biomarkers, <1,000 biomarkers, <500 biomarkers, <200 biomarkers, <100 biomarker, <50 biomarkers, etc.).

In some embodiments, expression products are mRNAs corresponding to the biomarkers of the panel. In some embodiments, detecting the levels of expression products comprises exposing the sample to nucleic acid probes complementary to the mRNAs corresponding to the biomarkers of the panel. In some embodiments, nucleic acid probes are covalently linked to a solid surface. In some embodiments, detecting the levels of expression products comprises use of a detection technique selected from the group consisting of microarray analysis, reverse transcriptase PCR, quantitative reverse transcriptase PCR, and hybridization analysis.

In some embodiments, detection of expression products comprises generation of cDNA (e.g., by reverse transcription) from the mRNA (e.g., biomarker mRNA) in a sample, and detecting the cDNA. In some embodiments, cDNA are full-length cDNA. In some embodiments, cDNA is further amplified prior to detection (e.g., by qPCR). In some embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA may be detected or used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

In some embodiments, expression products are proteins corresponding to the biomarkers of the panel. In some embodiments, detecting the levels of expression products comprises exposing the sample to antibodies for the proteins corresponding to the biomarkers of the panel. In some embodiments, antibodies are covalently linked to a solid surface. In some embodiments, detecting the levels of expression products comprises exposing the sample to a mass analysis technique (e.g., mass spectrometry).

In some embodiments, the present invention provides kits, reagent mixtures, and/or surfaces comprising (or displaying) reagents for detecting a panel of multiple biomarkers listed in Table 1. In some embodiments, reagents are provided for detection of 100 or fewer PTSD biomarkers (e.g., <100 biomarkers, <50 biomarkers, <40 biomarkers, <30 biomarkers, <20 biomarkers, <10 biomarkers). In some embodiments, reagents are provided for detection of two of more PTSD biomarkers (e.g., >3 biomarkers, >4 biomarkers, >5 biomarkers, >6 biomarkers, >7 biomarkers, >8 biomarkers, >9 biomarkers, >10 biomarkers, >15 biomarkers, >20 biomarkers, >30 biomarkers, >40 biomarkers). In some embodiments, the PTSD detecting reagents are provided with reagents for detection of other non-PTSD biomarkers (e.g., biomarkers that for other diseases or conditions). In some embodiments, reagents are proved for detecting less than 10,000 PTSD biomarkers and non-PTSD biomarkers combined (e.g., <5,000 biomarkers, <1,000 biomarkers, <500 biomarkers, <200 biomarkers, <100 biomarker, <50 biomarkers, etc.).

In some embodiments, reagents are provided to detect a panel of PTSD biomarkers comprising one or more of SERPINB1, LILRB3, and GLRX. In some embodiments, reagents are provided to detect a panel of PTSD biomarkers comprising one or more of IFI27, FUOM, HSPA8, IGK, LCMT1, THYN1, SEC14L2, SLC16A3, SERINC2, TRPM6, and XKRX. In some embodiments, the panel further comprises one or more of CYP21A1, ADN, DGAT2, PROK2, TNFRSF1A and ELOVL5. In some embodiments, reagents are provided to detect a panel of PTSD biomarkers comprising one or more of IFI27, FUOM, HSPA8, IGK, LCMT1, THYN1, SEC14L2, SLC16A3, SERINC2, TRPM6, XKRX, CYP21A1, ADN, DGAT2, PROK2, TNFRSF1A and ELOVL5.

In some embodiments, reagents are provided for the detection and/or quantification of biomarker proteins. Suitable reagents include primary antibodies (e.g., that bind to the biomarkers), secondary antibodies (e.g., that bind primary antibodies), antibody fragments, aptamers, etc. Protein detection reagents may be labeled (e.g., fluorescently) or unlabeled, and may by free in solution or immobilized.

In some embodiments, reagents are provided for the detection and/or quantification of biomarker protein (e.g., mRNA). Suitable reagents include amplification and/or detection reagents, such as primers and/or probes. Primers and probes may be labeled (e.g., fluorescently) or unlabeled, and may by free in solution or immobilized.

In some embodiments, the present invention provides methods comprising: (a) receiving a sample obtained from a subject; (b) detecting in the sample one or more biomarkers listed in Table 1; and (c) converting the data generated in step (b) into a PTSD risk assessment for the human subject. In some embodiments, additional steps are performed, including but not limited to one or more of: generating a report, diagnosing the subject with PTSD, recommending a course of therapy, administering a therapy (e.g., treating with a drug, treating with psychotherapy, etc.), etc.

In some embodiments, the present invention provides methods for characterizing a sample as having been obtained from a human subject suffering from PTSD, the method comprising one or more (e.g., all) of the steps of: (a) receiving a sample obtained from the subject; (b) detecting in the sample the level of a first biomarker of PTSD selected from the biomarkers listed in Table 1; (c) detecting in the sample the level of at least a second biomarker of PTSD selected from the biomarkers listed in Table 1; (d) using a computer-based analysis program is used to convert the data generated in steps (b) and (c) into a PTSD risk assessment for the human subject from which the sample was obtained; and (e) generating a report characterizing the sample as having been obtained from a human subject likely suffering from PTSD based on the risk assessment of step (d).

In some embodiments, the present invention provides methods of testing a subject for PTSD, comprising: (a) obtaining a sample from the subject; (b) providing (e.g., delivering, shipping, etc.) the sample to testing facility to be tested for levels expression products corresponding to a panel of multiple biomarkers listed in Table 1; and (c) receiving a report from the testing facility indicating the likelihood of the subject suffering from PTSD. In some embodiments, methods further comprise a step of providing a kit to collect the samples.

A method of detecting determining the levels of one or more biomarkers listed in Table 1 in a biological sample from a subject suffering from a post-traumatic stress state, the method comprising: quantifying the levels of the one or more biomarkers listed in Table 1 in the biological sample from said subject suffering from a post-traumatic stress state. In some embodiments, quantifying the levels of the one or more biomarkers listed in Table 1 comprises determining the level or concentration of the biomarkers. In some embodiments, quantifying the levels of expression of the one or more biomarkers listed in Table 1 comprises determining the level or concentration of the biomarkers. In some embodiments, the biomarker RNA is quantified. In some embodiments, the biomarker protein is quantified. In some embodiments, the biological sample is blood or saliva.

A method of treating post-traumatic stress in a subject comprising (a) determining the levels of one or more biomarkers listed in Table 1 in a biological sample from a subject, and (b) administering a therapy for post-traumatic stress. In some embodiments, therapy is selected from the group consisting of psychoanalysis, psychotherapy, and pharmacological treatment.

In some embodiments, post-traumatic stress biomarkers are proteins or protein subunits (See, e.g., Table 1) the concentration of which in a biological sample (e.g., blood, saliva, urine, tissues, etc.) are altered when compared to a control. In some embodiments, protein detection and/or quantification reagents are provided. In embodiments in which a biomarker is a protein, polypeptide and/or peptide, detection and/or quantification reagents may comprise antibodies or antibody-like reagents, aptamers, etc. that bind (e.g., specifically) to the biomarker(s). In such embodiments, detection and/or quantification may be achieved by, for example, an immunoassay, Western blot, enzyme-linked immunosorbent assay (ELISA), radioimmunoassay (RIA), fluorimetric assay, or other suitable assays known in the field.

In some embodiments, post-traumatic stress biomarkers are RNAs (e.g., mRNA) (See, e.g., Table 1), the level of expression of which are indicative of post-traumatic stress states. In embodiments in which a biomarker is an RNA (e.g., mRNA), detection and/or quantification reagents may comprise primers (e.g., for amplification, reverse transcription, etc.) or probes (e.g., detectably-labeled (e.g., optically-labeled, fluorescently labeled, etc.) oligonucleotides) that bind (e.g., specifically) to the biomarker. In such embodiments, detection and/or quantification may be achieved by, for example, RT-PCR, qPCR, dPCR, Northern blot analysis, an enzymatic cleavage assay (e.g., INVADER, Hologic, Inc.; See e.g., U.S. Pat. Nos. 5,846,717, 6,090,543; 6,001,567; 5,985,557; and 5,994,069; each of which is herein incorporated by reference), a hybridization assay (e.g., TaqMan assay (Life Technologies; See e.g., U.S. Pat. Nos. 5,962,233 and 5,538,848, each of which is herein incorporated by reference), etc.

Definitions

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition.

As used herein, the term "sample" is used in its broadest sense. In one sense it can refer to biological samples obtained from animals (including humans) and encompass fluids, solids, tissues (e.g., neurological tissue), and gases. Biological samples include blood products (e.g., plasma and serum), saliva, urine, and the like. These examples are not to be construed as limiting the sample types applicable to the present invention.

As used here, the term "antibody" includes monoclonal antibodies (including full length monoclonal antibodies), polyclonal antibodies, multi specific antibodies (e.g., bispecific antibodies), humanized antibodies, and antibody fragments so long as they exhibit the desired biological activity. Antibodies can be conjugated to other molecules. As used herein, the term "antibody fragments" refers to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments.

The terms "specific binding" or "specifically binding" when used in reference to the interaction of capture or detection reagent (e.g., antibody, probe etc.) and a target or biomarker (e.g., protein, DNA, RNA, etc.) means that the interaction is dependent upon the presence of a particular structure (i.e., the antigenic determinant or epitope; the nucleic acid sequence).

As used herein, the terms "non-specific binding" and "background binding" when used in reference to the interaction capture or detection reagent (e.g., antibody probe etc.) and a target or biomarker (e.g., protein, DNA, RNA, etc.) refer to an interaction that is not dependent on the presence of a particular structure or sequence.

As used herein, "a reagent that specifically detects expression levels" refers to reagents used to detect the expression of one or more genes (e.g., including but not limited to, the biomarkers herein). Examples of suitable reagents include but are not limited to, nucleic acid probes capable of specifically hybridizing to the gene of interest, aptamers, PCR primers capable of specifically amplifying the gene of interest, and antibodies capable of specifically binding to proteins expressed by the gene of interest.

As used herein, the term "nucleic acid detection assay" refers to any method of determining the nucleotide composition of a nucleic acid of interest. Nucleic acid detection assay include but are not limited to, DNA sequencing methods, probe hybridization methods, enzyme mismatch cleavage methods (e.g., Variagenics, U.S. Pat. Nos. 6,110,684, 5,958,692, 5,851,770, herein incorporated by reference in their entireties); polymerase chain reaction; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Barnay Proc. Natl. Acad. Sci USA 88, 189-93 (1991)); and sandwich hybridization methods (e.g., U.S. Pat. No. 5,288,609, herein incorporated by reference in its entirety).

The term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as a DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, a "diagnostic" test application includes the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition.

DETAILED DESCRIPTION

The present invention relates generally to the detection or diagnosis of post-traumatic stress states in a subject, and provides methods, reagents, and kits useful for this purpose. Provided herein are biomarkers that are indicative of and/or diagnostic of PTSD. PTSD involves a failure in recovery and restitution of physiological homeostasis, possibly resulting from individual vulnerability to stress-related biological processes; although the present invention is not limited to any particular cause of PTSD and an understanding of the cause of PTSD is not necessary to practice the present invention. In certain embodiments, the present invention provides a panel of biomarkers (e.g., blood biomarkers (e.g., genes that are over or under expressed in a PTSD state), etc.) that indicate prolonged response to chronic stress. The panel has been identified in animal models, whereby the prolonged post-stress changes in the blood of an animal that is known to show depressive behavior, in comparison to other control strains, is an indication of posttraumatic stress states.

Experiments were conducted during development of embodiments of the present invention to generate a panel of PTSD markers using chronic stress and different animal strains. Strains of animals that are known to show greater depressive-like behavior or vulnerability to stress, and control strains were exposed to a chronic stress paradigm. Genome-wide gene expression in the blood of animals exposed to no stress (NS) was compared to expression in animals exposed to prolonged chronic restraint stress, either during the stress (chronic resistant stress (CRS)) or 10 days post-stress (PCRS). In some embodiments, genes that have altered expression (e.g., increased or decreased) during stress and remain altered 10 days after the chronic stress in a stress-reactive strain, but not in a "resilient" strain are determined to be predictors of failure in recovery or reinstitution of physiological homeostasis. In some embodiments, genes that have altered expression (e.g., increased or decreased) post-stress compared to both the no stress control and during the stress in a stress-reactive strain, but not in a "resilient" strain are determined to be predictors of failure in recovery or reinstitution of physiological homeostasis.

Genome-wide gene expression in the amygdala and the hippocampus of animals exposed to no stress (NS) was also compared to expression in animals exposed to prolonged chronic restraint stress, either during the stress (chronic resistant stress (CRS)) or 10 days post-stress (PCRS). In some embodiments, genes that have altered expression (e.g., increased or decreased) during stress and remain altered 10 days after the chronic stress in a stress-reactive strain, but not in a "resilient" strain are determined to be predictors of failure in recovery or reinstitution of physiological homeostasis. In some embodiments, genes that have altered expression (e.g., increased or decreased) post-stress compared to both the no stress control and during the stress in a stress-reactive strain, but not in a "resilient" strain are determined to be predictors of failure in recovery or reinstitution of physiological homeostasis. Those genes that share significant expression differences between these stress states in the blood and in the amygdala or hippocampus are markers of post traumatic stress states.

In some embodiments, the present invention provides biological markers indicative of a post-traumatic stress state in a subject. In some embodiments, the presence of such biomarkers (e.g., elevated or reduced expression of biomarker genes) is indicative of and/or diagnostic of a prolonged response to stress (e.g., chronic stress). In some embodiments, biological markers are indicative of and/or diagnostic of PTSD. In some embodiments, biological markers are blood biomarkers. In some embodiments, the present invention provides one or more biomarkers, or a panel of biological markers, that can be identified from tissue or blood or other sample types. In some embodiments, these biological markers show increased or decreased levels of gene-specific RNA in subjects with current symptoms (e.g., PTSD symptoms) compared to those of controls (e.g., a subject who has experienced chronic stress without developing PTSD, a subject not exposed to chronic stress, etc.). In some embodiments, these biological markers show increased or decreased levels of protein expressed from these genes in subjects with current symptoms (e.g., PTSD symptoms) compared to those of controls (e.g., a subject who has experienced chronic stress without developing PTSD, a subject not exposed to chronic stress, etc.).

In some embodiments, a subject to be tested by the methods and reagents described herein exhibits one or more symptoms of post-traumatic stress and/or has one or more risk factors for PTSD. Symptoms of PTSD include, for example: intrusive memories (e.g., recurrent, unwanted distressing memories of the traumatic event; reliving the traumatic event as if it were happening again (flashbacks); upsetting dreams about the traumatic event; severe emotional distress or physical reactions to something that reminds the subject of the event, etc.), avoidance (e.g., trying to avoid thinking or talking about the traumatic event; avoiding places, activities or people that remind the subject of the traumatic event; etc.), negative changes in thinking and mood (e.g., negative feelings about self or others; inability to experience positive emotions; feeling emotionally numb; lack of interest in activities the subject once enjoyed; hopelessness about the future; memory problems, including not remembering important aspects of the traumatic event; difficulty maintaining close relationships; etc.), changes in emotional reactions (e.g., irritability, angry outbursts or aggressive behavior; always being on guard for danger; overwhelming guilt or shame; self-destructive behavior, such as drinking too much or driving too fast; trouble concentrating; trouble sleeping; being easily startled or frightened; etc.), etc. Risk factors of PTSD include, for example: experiencing intense or long-lasting trauma; having experienced other trauma earlier in life, including childhood abuse or neglect; having a job that increases your risk of being exposed to traumatic events, such as military personnel and first responders; having other mental health problems, such as anxiety or depression; lacking a good support system of family and friends; having biological relatives with mental health problems, including PTSD or depression; etc. In some embodiments, prior to, concurrent with, and/or following testing a subject for PTSD biomarkers according to embodiments described herein, a subject is evaluated for symptoms and/or risk factors of post-traumatic stress.

In some embodiments, biomarkers provide confirmation that a subject's symptoms are the result of PTSD. In other embodiments, biomarkers predict whether a subject who has experienced chronic stress will develop PTSD at a later time. In some embodiments, biomarkers predict whether a subject will develop PTSD after experiencing a traumatic event. In some embodiments, biomarkers allow diagnosis of PTSD in a subject not actively experiencing symptoms or unable to communicate such symptoms. In some embodiments, biomarkers differentiate between a subject experiencing symptoms caused by current chronic stress and those caused by PTSD.

The present invention relates to the biomarkers of Table 1 and/or the use thereof in detecting, characterizing, identifying, and/or diagnosing prolonged responses to chronic stress in a subject. Experiments were conducted during development of embodiments of the present invention to identify biomarkers that are indicative and/or diagnostic of PTSD. In some embodiments, biomarkers of column 1 of Table 1 find use in diagnosis and/or characterization of PTSD. In some embodiments, biomarkers of column 1 of Table 1, when altered in a subject experiencing stress or following stress (e.g., compared to control, compared to a threshold level, etc.), are indicative of PTSD. In some embodiments, biomarkers of column 2 of Table 1 find use in diagnosis and/or characterization of PTSD. In some embodiments, biomarkers of column 2 of Table 1, when altered in a subject post-stress but not during stress (e.g., compared to control, compared to a threshold level, etc.), are indicative of PTSD. In some embodiments, biomarkers of column 3 of Table 1 find use in diagnosis and/or characterization of PTSD. In some embodiments, biomarkers of column 3 of Table 1, when altered in a subject post-stress but not during stress (e.g., compared to control, compared to a threshold level, etc.), are indicative of PTSD. In some embodiments, biomarkers of column 4 of Table 1 find use in diagnosis and/or characterization of PTSD. In some embodiments, biomarkers of column 4 of Table 1, when altered in a subject post-stress but not during stress (e.g., compared to control, compared to a threshold level, etc.), are indicative of PTSD. In some embodiments, biomarkers of column 5 of Table 1 find use in diagnosis and/or characterization of PTSD. In some embodiments, biomarkers of column 5 of Table 1, when altered in a subject post-stress but not during stress (e.g., compared to control, compared to a threshold level, etc.), are indicative of PTSD. In some embodiments, biomarkers of column 6 of Table 1 find use in diagnosis and/or characterization of PTSD. In some embodiments, biomarkers of column 6 of Table 1, when altered in a subject post-stress but not during stress (e.g., compared to control, compared to a threshold level, etc.), are indicative of PTSD. In some embodiments, a panel of biomarkers for characterization and/or diagnosis of PTSD comprises biomarkers from one or more columns of Table 1 (e.g., a single column, two columns, three columns, four columns, five columns, six columns). In some embodiments, altered expression (e.g., as evidenced by altered mRNA level, protein level, etc. compared to a threshold or control value).

In some embodiments, the present invention provides one or more biomarkers listed in Table 1 or a particular column or set of columns therein (e.g., column 6, columns 5 and 6, etc.). In some embodiments, the present invention provides a panel of biomarkers comprising a plurality (e.g., 2, 3, 4, 5, 6, 7, 8, 9, 10 . . . 15 . . . 20 . . . 30 . . . 40, or more) of biomarkers listed in Table 1 (or a particular column or set of columns therein (e.g., column 6, columns 5 and 6, etc.). In some embodiments the present invention provides a panel of reagents for detecting mRNAs or encoded proteins comprising one or more genes from Table 1 (or a particular column or set of columns therein (e.g., column 6, columns 5 and 6, etc.). In some embodiments the present invention provides a panel of reagents for detecting mRNAs or encoded proteins consisting of one or more genes from Table 1 (or a particular column or set of columns therein (e.g., column 6, columns 5 and 6, etc.). In some embodiments, a panel comprises one or more reagents for detecting mRNAs or encoded proteins from Table 1 and one or more additional genes. In some embodiments, the present invention provides a set of genes whose mRNA levels differ in (e.g., in the blood of) subjects showing higher and lower level of prolonged response to stress (e.g., PTSD). In some embodiments, the present invention provides a set of genes whose protein levels differ in (e.g., in the blood of) subjects showing higher and lower level of prolonged response to stress (e.g., PTSD). In some embodiments, the present invention provides biological markers that are common between those expressed in the blood and those expressed in the brain regions of animals, showing higher and lower level of prolonged response to stress (e.g., PTSD). In some embodiments of the present invention, the expression of one or more such genes are used to diagnose or suggest a risk of PTSD from human sample (e.g., blood sample). In some embodiments, the presence of a gene or panel of genes (or altered transcript levels of such genes) that correlates with PTSD (e.g., is indicative of PTSD, is diagnostic of PTSD) allows a treating physician to take any number of courses of action, including, but not limited to, further diagnostic assessment, selection of appropriate treatment (e.g., pharmacological, nutritional, counseling, and the like), increased or decreased monitoring, etc. In some embodiments, changes in expression of a gene or panel of genes that correlates with PTSD (e.g., is indicative of PTSD, is diagnostic of PTSD) allows a treating physician to take any number of courses of action, including, but not limited to, further diagnostic assessment, selection of appropriate treatment (e.g., pharmaceutical, nutritional, counseling, and the like), increased or decreased monitoring, etc.

In some embodiments the present invention provides a method for detecting or assessing the risk of prolonged response to chronic stress (e.g., PTSD) in a subject. In some embodiments the present invention provides a method for diagnosing PTSD in a subject. In some embodiments, the biomarkers provided herein are used in conjunction with other evidence of PTSD (e.g., symptoms, risk factors, etc.) in making a diagnosis. In some embodiments, the biomarkers provided herein are used in the absence of other evidence of PTSD (e.g., symptoms) in making a diagnosis.

In some embodiments the present invention provides methods for characterizing the level of gene expression of a panel of genes comprising detecting the amount of mRNA of a panel of genes of one or more of the genes listed in Table 1 (or a particular column or set of columns therein (e.g., column 6, columns 5 and 6, etc.). In some embodiments, the panel comprises 1, 2, 3, 4, 5, 6, 7, 8, 9, 10, 11, 12, 13, 14, 15, 16, 17, 18, 19, 20 . . . 30 . . . 40, or more genes. In some embodiments the present invention provides methods comprising the step of exposing a sample to nucleic acid probes complementary to the mRNA of a panel of genes selected from the genes listed in Table 1 (or a particular column or set of columns therein (e.g., column 6, columns 5 and 6, etc.). In some embodiments the methods employ a nucleic acid detection technique (e.g., microarray analysis, reverse transcriptase PCR, quantitative reverse transcriptase PCR, and hybridization analysis).

In some embodiments the present invention provides methods for characterizing the level of gene expression of a panel of genes by detecting the amount of protein (e.g., in the blood) corresponding to one or more of the genes listed in Table 1. In some embodiments, a panel comprises 1, 2, 3, 4, 5, 6, 7, 8, 9, 10, 11, 12, 13, 14, 15, 16, 17, 18, 19, 20 . . . 30 . . . 40, etc. genes. In some embodiments the present invention provides methods comprising the step of exposing a sample to antibodies (or antibody fragments, or aptamers, etc.) for the proteins corresponding to one or more of the genes listed in Table 1. In some embodiments, detecting a change in the expression of one or more of the genes listed in Table 1 comprises exposing a sample (e.g., blood sample) to antibodies (or antibody fragments, or aptamers, etc.) specific to the biomarkers and detecting binding to the biomarkers. In some embodiments the present invention provides a method for detecting prolonged response to chronic stress (e.g., PTSD) in a human subject.

In some embodiments, biomarkers for use in a panel and/or in an assay for characterization/diagnosis of PTSD are selected from SERPINB1, LILRB3, and GLRX (e.g., one or more of those markers alone or in combination with other markers from Table 1 or genes known in the field). In some embodiments, altered expression (e.g., consistent with experiments conducted during development of embodiments of the present invention) of one or more of SERPINB1, LILRB3, and GLRX is indicative and/or diagnostic of prolonged stress response (e.g., PTSD).

In some embodiments, biomarkers for use in a panel and/or in an assay for characterization/diagnosis of PTSD are selected from IFI27, FUOM, HSPA8, IGK, LCMT1, THYN1, SEC14L2, SLC16A3, SERINC2, TRPM6, and XKRX (e.g., one or more of those markers alone or in combination with other markers from Table 1 (e.g., one or more of SERPINB1, LILRB3, and GLRX) or genes known in the field). In some embodiments, the panel further comprises one or more of CYP21A1, ADN, DGAT2, PROK2, TNFRSF1A and ELOVL5. In some embodiments, altered expression (e.g., consistent with experiments conducted during development of embodiments of the present invention) of one or more of IFI27, FUOM, HSPA8, IGK, LCMT1, THYN1, SEC14L2, SLC16A3, SERINC2, TRPM6, and XKRX is indicative and/or diagnostic of prolonged stress response (e.g., PTSD). In some embodiments, altered expression (e.g., consistent with experiments conducted during development of embodiments of the present invention) of one or more of CYP21A1, ADN, DGAT2, PROK2, TNFRSF1A and ELOVL5 is indicative and/or diagnostic of prolonged stress response (e.g., PTSD).

In some embodiments the present invention relates to gene expression profiles (e.g., increases and/or decrease in the expression of multiple genes) that correlate with prolonged response to chronic stress (e.g., PTSD), and uses thereof. In some embodiments, a panel of two or more genes is analyzed (e.g., 2 genes . . . 4 genes . . . 6 genes . . . 8 genes . . . 10 genes . . . 15 genes . . . 20 genes . . . 30 genes, or more.). In some embodiments, detection and/or quantification reagents (e.g., oligonucleotide probes) are provided that have specificity for genes associated prolonged response to chronic stress (e.g., PTSD) (See, e.g., genes identified in Table 1).

In some embodiments, the present invention provides a panel of biomarkers for the detection, characterization, and/or diagnosis of a variety of diseases and/or conditions (e.g., psychiatric conditions, mental disease, genetic conditions, physical diseases, etc.), one of which is PTSD. In certain embodiments, a panel comprises multiple biomarkers from Table 1 (e.g., column 6, column 5, etc.) in addition to biomarkers for other diseases or conditions (e.g., depression, anxiety, etc.). In particular embodiments, testing a subject (e.g., a blood sample from a subject) for such a panel allows diagnosis of PTSD in addition to other diseases, conditions, or disorders. In some embodiments, all the biomarkers on the panel are provided for a diagnostic or other medical purpose.

It is contemplated that a test sample (e.g., containing isolated and/or purified biomarker protein and/or RNA, containing test reagents, etc.) is prepared from biological (e.g., saliva, blood, etc.) samples from subject (e.g., with PTSD), and the test samples are applied to the panel. It is contemplated that the differential hybridization of the patient samples relative to the control samples provides an expression signature of PTSD. In some embodiments, gene expression from a test sample is compared with a prior sample from the same patient to monitor changes over time. In some embodiments, gene expression from a test sample is compared with a sample from the patient under a treatment regimen (e.g., pharmaceutical therapy) to test or monitor the effect of the therapy. In some embodiments, gene expression from a test sample is compared to gene expression from a negative control sample (e.g., a subject known to not have PTSD). In some embodiments, gene expression levels from a test sample are compared to predetermined threshold levels identified (e.g., based on population averages for patients with similar age, gender, metabolism, etc.) as "normal" for individuals without PTSD. In some embodiments, an increase or decrease of greater than 1.1-fold (e.g., 1.2-fold, 1.5-fold, 2-fold, 3-fold, 5-fold, 10-fold, or higher) compared to "normal" levels or any increase over a normal level or threshold level is indicative of and/or diagnostic for PTSD. In some embodiments, separate indicative and diagnostic thresholds are established.

The level of biomarker(s) present in a sample may be assessed on an absolute basis or a relative basis. When assessed on a relative basis, comparison may be made to controls including but not limited to a historical sample from the same patient (e.g., serial samples, longitudinal samples); level(s) found in a patient or population of patients absent of disease or disorder; a threshold value; and acceptable range; etc.

In some embodiments, provided herein are DNA-, RNA- and protein-based diagnostic methods that either directly or indirectly detect the biomarkers described herein. The present invention also provides compositions, reagents, and kits for such diagnostic purposes. The diagnostic methods described herein may be qualitative or quantitative. Quantitative diagnostic methods may be used, for example, to compare a detected biomarker level to a cutoff or threshold level. Where applicable, qualitative or quantitative diagnostic methods may also include amplification of target, signal or intermediary.

In some embodiments, biomarkers are detected at the nucleic acid (e.g., RNA) level. For example, the amount of biomarker RNA (e.g., mRNA) present in a sample is determined (e.g., to determine the level of biomarker expression). Biomarker nucleic acid (e.g., RNA, amplified cDNA, etc.) may be detected/quantified using a variety of nucleic acid techniques known to those of ordinary skill in the art, including but not limited to nucleic acid sequencing, nucleic acid hybridization, and nucleic acid amplification.

In some embodiments, a microarray is used to detect nucleic acid biomarkers (e.g., those of Table 1). Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is typically a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

Genomic DNA and mRNA may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. In some embodiments, PCR is digital PCR, see, e.g., Vogelstein, B., & Kinzler, K. W. (1999) "Digital PCR" Proc. Natl. Acad. Sci. USA 96:9236-9241; herein incorporated by reference in its entirety. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

Non-amplified or amplified nucleic acids can be detected by any conventional means. For example, in some embodiments, nucleic acids are detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

In some embodiments, quantitative PCR (qPCR) is utilized, e.g., using SYBR Green dye on an Applied Biosystems 7300 Real Time PCR system essentially as described (Chinnaiyan et al., Cancer Res 65, 3328 (2005); Rubin et al., Cancer Res 64, 3814 (2004); herein incorporated by reference in its entirety).

In some embodiments, nucleic acid from a sample is sequenced (e.g., in order to detect biomarkers). Nucleic acid molecules may be sequence analyzed by any number of techniques. The analysis may identify the sequence of all or a part of a nucleic acid. Illustrative non-limiting examples of nucleic acid sequencing techniques include, but are not limited to, chain terminator (Sanger) sequencing and dye terminator sequencing, as well as "next generation" sequencing techniques. Those of ordinary skill in the art will recognize that because RNA is less stable in the cell and more prone to nuclease attack, experimentally RNA is usually, although not necessarily, reverse transcribed to DNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the systems, devices, and methods employ parallel sequencing of partitioned amplicons (PCT Publication No: WO2006084132 to Kevin McKernan et al., herein incorporated by reference in its entirety). In some embodiments, DNA sequencing is achieved by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties) the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties) and the Adessi PCR colony technology (Adessi et al. (2000). Nucleic Acid Res. 28, E87; WO 00018957; herein incorporated by reference in its entirety).

A set of methods referred to as "next-generation sequencing" techniques have emerged as alternatives to Sanger and dye-terminator sequencing methods (Voelkerding et al., Clinical Chem., 55: 641-658, 2009; MacLean et al., Nature Rev. Microbiol., 7: 287-296; each herein incorporated by reference in their entirety). Next-generation sequencing (NGS) methods share the common feature of massively parallel, high-throughput strategies, with the goal of lower costs in comparison to older sequencing methods. NGS methods can be broadly divided into those that require template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, Pacific Biosciences (PAC BIO RS II) and other platforms commercialized.

In some embodiments, provided herein are methods for isolating DNA or RNA from a biological sample. Methods may comprise steps of homogenizing a sample in a suitable buffer, removal of contaminants and/or assay inhibitors adding a target capture reagent (e.g., a magnetic bead to which is linked an oligonucleotide complementary to the target), incubated under conditions that promote the association (e.g., by hybridization) of the target with the capture reagent to produce a target:capture reagent complex, incubating the target:capture complex under target-release conditions. In some embodiments, multiple biomarker targets are isolated in each round of isolation by adding multiple target capture reagents (e.g., specific to the desired biomarkers) to the solution. For example, multiple target capture reagents, each comprising an oligonucleotide specific for a different biomarker target can be added to the sample for isolation of multiple targets. It is contemplated that the methods encompass multiple experimental designs that vary both in the number of capture steps and in the number of targets captured in each capture step. In some embodiments, capture reagents are molecules, moieties, substances, or compositions that preferentially (e.g., specifically and selectively) interact with a particular biomarker sought to be isolated, purified, detected, and/or quantified. Any capture reagent having desired binding affinity and/or specificity to the analyte target can be used in the present technology. For example, the capture reagent can be a macromolecule such as a peptide, a protein (e.g., an antibody or receptor), an oligonucleotide, a nucleic acid, (e.g., nucleic acids capable of hybridizing with the target nucleic acids), vitamins, oligosaccharides, carbohydrates, lipids, or small molecules, or a complex thereof. As illustrative and non-limiting examples, an avidin target capture reagent may be used to isolate and purify targets comprising a biotin moiety, an antibody may be used to isolate and purify targets comprising the appropriate antigen or epitope, and an oligonucleotide may be used to isolate and purify a complementary oligonucleotide.

Any nucleic acids, including single-stranded and double-stranded nucleic acids, that are capable of binding, or specifically binding, to the target can be used as the capture reagent. Examples of such nucleic acids include DNA, RNA, aptamers, peptide nucleic acids, and other modifications to the sugar, phosphate, or nucleoside base. Thus, there are many strategies for capturing a target and accordingly many types of capture reagents are known to those in the art.

In addition, target capture reagents comprise a functionality to localize, concentrate, aggregate, etc. the capture reagent and thus provide a way to isolate and purify the target biomarker when captured (e.g., bound, hybridized, etc.) to the capture reagent (e.g., when a target:capture reagent complex is formed). For example, in some embodiments the portion of the target capture reagent that interacts with the target (e.g., the oligonucleotide) is linked to a solid support (e.g., a bead, surface, resin, column, and the like) that allows manipulation by the user on a macroscopic scale. Often, the solid support allows the use of a mechanical means to isolate and purify the target:capture reagent complex from a heterogeneous solution. For example, when linked to a bead, separation is achieved by removing the bead from the heterogeneous solution, e.g., by physical movement. In embodiments in which the bead is magnetic or paramagnetic, a magnetic field is used to achieve physical separation of the capture reagent (and thus the target) from the heterogeneous solution. Magnetic beads used to isolate targets are described in the art, e.g., as described in European Patent Application No. 87309308, incorporated herein in its entirety for all purposes.

In some embodiments, a computer-based analysis program is used to translate the raw data generated by the detection assay (e.g., the presence, absence, or amount of expression a panel of genes) into data of predictive value for a clinician (e.g., a risk score, a qualitative description, etc.). In some embodiments, data analysis produces a PTSD risk or likelihood score. In some embodiments, data analysis produces a PTSD diagnosis. In some embodiments, computer analysis combines the data from numerous biomarkers into a single score or value that is predictive and/or diagnostic for PTSD.

In some embodiments, a clinician accesses the data and/or analysis thereof using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personal, and subjects. For example, in some embodiments of the present invention, a sample (e.g., a biopsy or a blood, serum or saliva sample) is obtained from a subject and submitted to a profiling service (e.g., clinical lab at a medical facility, third-party testing service, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a blood or saliva sample, a urine sample, etc.) and directly send it to a profiling center. Where the sample also comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (e.g., expression data), specific for the diagnostic or prognostic information desired for the subject.

In some embodiments, profile data is prepared in a format suitable for interpretation by a treating clinician and/or the test subject. For example, rather than providing raw expression data, the prepared format may represent a diagnosis or risk assessment (e.g., likelihood of subject having PTSD) for the subject. Recommendations for particular treatment options may also be provided. The data may be displayed to the clinician by any suitable method. For example, in some embodiments, the profiling service generates a report that can be printed for the clinician (e.g., at the point of care) or displayed to the clinician on a computer monitor.

In some embodiments, a report is generated (e.g., by a clinician, by a testing center, by a computer or other automated analysis system, etc.). A report may contain test results, diagnoses (e.g., PTSD, high likelihood of PTSD, sever PTSD, etc.), and/or treatment recommendations (e.g., psychoanalysis, psychotherapy, pharmaceutical treatment, observation, etc.).

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may choose further intervention, treatment, and/or counseling based on the results. In some embodiments, the data is used for research use. For example, the data may be used to further optimize the inclusion or elimination of markers as more or less useful indicators of PTSD (e.g., in a particular population (e.g., children, adolescents, adults, males, females, etc.).

Compositions for use in the diagnostic methods of the present invention include, but are not limited to, probes, amplification oligonucleotides, and antibodies. Particularly preferred compositions detect the level of expression (e.g., blood mRNA level, blood protein level) of a panel of genes. Systems and kits are provided that are useful, necessary, and/or sufficient for detecting expression of one or more genes.

Any of these compositions, alone or in combination with other compositions of the present invention, may be provided in the form of a kit or reagent mixture. For example, labeled probes and primer pairs are provided in a kit for the amplification and detection and/or quantification of a panel of genes selected from those listed in Table 1. Kits may include any and all components necessary or sufficient for assays including, but not limited to, detection reagents, amplification reagents, buffers, control reagents (e.g., tissue samples, positive and negative control sample, etc.), solid supports, labels, written and/or pictorial instructions and product information, inhibitors, labeling and/or detection reagents, package environmental controls (e.g., ice, desiccants, etc.), and the like. In some embodiments, kits provide a sub-set of the required components, wherein it is expected that the user will supply the remaining components. In some embodiments, the kits comprise two or more separate containers wherein each container houses a subset of the components to be delivered.

In some embodiments, the present invention provides therapies for diseases characterized by altered expression of disease markers identified using the methods of the present invention. In particular, the present invention provides methods and compositions for monitoring the effects of a candidate therapy and for selecting therapies for patients.

In some embodiments, methods of treating post-traumatic stress states are provided (e.g., following biomarker identification of a subject as suffering from post-traumatic stress). Suitable treatments include psychotherapy (e.g., cognitive therapy, exposure therapy, eye movement desensitization and reprocessing (EMDR), etc.) and medication (e.g., antidepressants (e.g., selective serotonin reuptake inhibitors (SSRI) such as sertraline and paroxetine), anti-anxiety medications, prazosin, etc.).

In some embodiments, systems and devices are provided for implementing the diagnostic methods described herein (e.g., data analysis, communication, result reporting, etc.). In some embodiments, a software or hardware component receives the results of multiple assays, factors, and/or biomarkers and determines a single value result to report to a user that indicates a conclusion (e.g., high risk PTSD, low risk of PTSD, PTSD diagnosis, etc.). Related embodiments calculate a risk factor based on a mathematical combination (e.g., a weighted combination, a linear combination) of the results from multiple assays, factors, and/or biomarkers.

Some embodiments comprise a storage medium and memory components. Memory components (e.g., volatile and/or nonvolatile memory) find use in storing instructions (e.g., an embodiment of a process as provided herein) and/or data. Some embodiments relate to systems also comprising one or more of a CPU, a graphics card, and a user interface (e.g., comprising an output device such as display and an input device such as a keyboard). Programmable machines associated with the technology comprise conventional extant technologies and technologies in development or yet to be developed (e.g., a quantum computer, a chemical computer, a DNA computer, an optical computer, a spintronics based computer, etc.). In some embodiments, the technology comprises a wired (e.g., metallic cable, fiber optic) or wireless transmission medium for transmitting data. For example, some embodiments relate to data transmission over a network (e.g., a local area network (LAN), a wide area network (WAN), an ad-hoc network, the internet, etc.). In some embodiments, programmable machines are present on such a network as peers and in some embodiments the programmable machines have a client/server relationship. In some embodiments, data are stored on a computer-readable storage medium such as a hard disk, flash memory, optical media, a floppy disk, etc.

In some embodiments, the technology provided herein is associated with a plurality of programmable devices that operate in concert to perform a method as described herein. For example, in some embodiments, a plurality of computers (e.g., connected by a network) may work in parallel to collect and process data, e.g., in an implementation of cluster computing or grid computing or some other distributed computer architecture that relies on complete computers (with onboard CPUs, storage, power supplies, network interfaces, etc.) connected to a network (private, public, or the internet) by a conventional network interface, such as Ethernet, fiber optic, or by a wireless network technology.

Some embodiments provide a computer that includes a computer-readable medium. The embodiment includes a random access memory (RAM) coupled to a processor. The processor executes computer-executable program instructions stored in memory. Such processors may include a microprocessor, an ASIC, a state machine, or other processor, and can be any of a number of computer processors, such as processors from Intel Corporation of Santa Clara, Calif. and Motorola Corporation of Schaumburg, Ill. Such processors include, or may be in communication with, media, for example computer-readable media, which stores instructions that, when executed by the processor, cause the processor to perform the steps described herein.

Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any suitable computer-programming language, including, for example, C, C++, C#, Visual Basic, Java, Python, Perl, and JavaScript.

Computers are connected in some embodiments to a network. Computers may also include a number of external or internal devices such as a mouse, a CD-ROM, DVD, a keyboard, a display, or other input or output devices. Examples of computers are personal computers, digital assistants, personal digital assistants, cellular phones, mobile phones, smart phones, pagers, digital tablets, laptop computers, internet appliances, and other processor-based devices. In general, the computers related to aspects of the technology provided herein may be any type of processor-based platform that operates on any operating system, such as Microsoft Windows, Linux, UNIX, Mac OS X, etc., capable of supporting one or more programs comprising the technology provided herein. Some embodiments comprise a personal computer executing other application programs (e.g., applications). The applications can be contained in memory and can include, for example, a word processing application, a spreadsheet application, an email application, an instant messenger application, a presentation application, an Internet browser application, a calendar/organizer application, and any other application capable of being executed by a client device.

All such components, computers, and systems described herein as associated with the technology may be logical or virtual.

EXPERIMENTAL

Example 1

Chronic Restraint Stress Experiments

Adult male Fisher 344, Brown-Norway, Lewis and Wistar Kyoto (WKY) rats were obtained from Harlan lab and were housed individually. The control, no stress (NS) group remained in their home cage. Two groups of rats were exposed to chronic restraint stress (CRS) in a breathable decapicone for two hours per day, for a two-week period. On the 15th day, CRS rats were tested in the elevated plus maze (EPM) test, and sacrificed immediately after by decapitation. The post-stress, PCRS group were placed back to their home cage for 10 days, after which they were tested in the EPM and sacrificed immediately. The NS control group went through EPM and decapitation in parallel with the CRS rats. Whole blood was collected into PAXgene blood RNA tubes. Whole amygdali and hippocampi were dissected from the brains.

Blood RNA, amygdala RNA and hippocampal RNA were obtained and reverse transcribed to synthesize full-length cDNA, followed by second strand cDNA synthesis. For each sample, in-vitro transcription (IVT) reactions were carried out incorporating biotinylated nucleotides according to the manufacturer's protocol for Illumina® Totalprep RNA amplification kit (Ambion). 1.5 µg biotin-labelled cRNA was then hybridized onto RatRef-12 Expression BeadChips (Illumina, San Diego Calif.) for 16 hours at 55° C. Post-hybridization staining and washing were performed according to manufacturer's protocols (Illumina). Illumina SENTRIX RatRef-12 v1.0 BeadChips were scanned using Illumina's BeadStation 500 scanner. Images were checked for grid alignment and then quantified using the BeadStudio software. Control summary graphs generated by BeadStudio were used as quality assurance tools for hybridization, washing stringency, and background. Integrity of the arrays was investigated using the array images. Mean pixel intensities by bead type, were created using BeadStudio v3.1.

Probe intensity data from Illumina Chip arrays were read into the R software environment directly from bead summary files produced by BeadStudio using the R/beadarray package. Quantile normalization was applied to the Illumina bead summary data using the R/preprocessCore package. Data quality was assessed using histograms of signal intensities, scatterplots, and hierarchical clustering of samples. Analysis of variance (ANOVA) methods were used to statistically resolve gene expression differences using the R/maanova package.

The comparison between the different control strains (F344, BN and LEW) and the strain with endogenous/genetically determined depressive behavior (WKY) was determined regarding the blood expression differences between NS versus CRS and PCRS groups (Column 1, Table 1) and at the PCRS versus the NS groups (Columns 2-6, Table 1). When the same comparisons were made for the amygdalar (A) or hippocampal (H) tissue, it was found that some of these differences are parallel to those in the blood. Therefore, the expression of these genes in the blood mirrors expression changes in these brain regions. These genes are marked in Table 1 with the superscript A and H.

The genes listed in Table 1 represent human genes, identified by their most frequently used names. The names of the rat orthologues are often different.

TABLE 1

Candidate blood markers for PTSD ($^A$ in amygdala, $^H$ in hippocampus as well)

| NS vs CRS & PCRS WKY | NS vs. PCRS | | | | |
|---|---|---|---|---|---|
| | WKY | F344 vs WKY | LEW vs WKY | BN vs WKY & LEW vs WKY | WKY vs ALL |
| ALOX15 | ACTA1 | ALG8 | C1QTNF7 | IFI27$^A$ | SERPINB1$^A$ |
| BCL11B | ACTN3 | APBA3 | CDH1 | FUOM | LILRB3$^A$ |
| CAT | ADN$^A$ | ARFIP1 | SLC9A9 | HSPA8 | GLRX |
| CDR2 | ADRP | ARL6 | DCAF17 | IGK | |
| EGLN2 | ATP6V1G1 | CCL28 | SSPN | LCMT1 | |
| EIF4G2 | BRD9 | CCR8 | MYOG | THYN1 | |

TABLE 1-continued

Candidate blood markers for PTSD ($^A$ in amygdala, $^H$ in hippocampus as well)

| NS vs CRS & PCRS WKY | NS vs. PCRS WKY | F344 vs WKY | LEW vs WKY | BN vs WKY & LEW vs WKY | WKY vs ALL |
|---|---|---|---|---|---|
| ELOVL5$^A$ | BZRP | COIL | PAK4 | SEC14L2 | |
| ETS1 | CKM | COPEB | PTPRM | SLC16A3 | |
| FECH | DEFA | CYP21A1$^H$ | RTKN | SERINC2 | |
| INPP5B | DGAT2$^A$ | DSCR3 | | TRPM6 | |
| IRF7 | FLOT2 | GPHA2 | | XKRX | |
| ITK | HNRPA3P2 | HOXD10 | | | |
| JAK1 | MIIP/IIP45 | HSD17B12 | | | |
| TMEM199 | CSTB | IER2 | | | |
| NPM1 | B9D2 | ALKBH4 | | | |
| PTP4A1 | SPTB | NUGGC | | | |
| RNF145 | HSD17B12 | IDI2 | | | |
| RPL41 | VOPP1 | FHOD1 | | | |
| SCD2 | STFA2 | TAGAP | | | |
| SV2B | PRR7 | DPH7 | | | |
| TRA29 | TPI1 | HTRA4 | | | |
| TESTIN | SWI5 | QPCT | | | |
| UBE2G1 | HSP8 | THSD4 | | | |
| USP25 | ATP5H | REPS2 | | | |
| ZFAND6 | MX2 | CD209 | | | |
| | NALP12 | GSTK1 | | | |
| | OAS1 | CPS1 | | | |
| | PI3 | G3PDH | | | |
| | PRDX6 | C3ORF49 | | | |
| | PROK2$^A$ | FAM107B | | | |
| | PSP | OTUD1 | | | |
| | CD302 | OSTM1 | | | |
| | RHOA | GLI4 | | | |
| | S100A8 | GCOM1 | | | |
| | SAS | TRIM60 | | | |
| | SLPI | LYG2 | | | |
| | TAPBPL | MAP3K3 | | | |
| | TNFRSF1A$^A$ | MCPT8L3 | | | |
| | TNNT3 | METTL2 | | | |
| | TPI1 | NGB | | | |
| | UBQLN1 | ODF1 | | | |
| | UGP2 | OPLAH | | | |
| | | P34 | | | |
| | | P4HA1 | | | |
| | | PHF13 | | | |
| | | PIAS1 | | | |
| | | PRM1 | | | |
| | | PVRL2 | | | |
| | | RALGDS | | | |
| | | RGS3 | | | |
| | | RPL34 | | | |
| | | RUNX1 | | | |
| | | SCAMP2 | | | |
| | | SEC61A2 | | | |
| | | SLC5A3 | | | |
| | | SOCS4 | | | |
| | | STAU1 | | | |
| | | SUSD3 | | | |
| | | SYNJ1 | | | |
| | | TSN | | | |
| | | USP49 | | | |
| | | VAPB | | | |
| | | WIF1 | | | |
| | | ZFYVE26 | | | |
| | | RNF114 | | | |

Genes listed above exhibited a change in blood transcript levels according to the following criteria, where "≠" indicates >25% difference in absolute transcript level, "=" indicates <25% difference in absolute transcript level:
Column 1: NS ≠ CRS = PCRS in WKY strain
Column 2: NS = CRS ≠ PCRS in WKY strain
Column 3: (PCRS − NS in WKY) ≠ (PCRS − NS in F344)
Column 4: (PCRS − NS in WKY) ≠ (PCRS − NS in LEW)
Column 5: (PCRS − NS in WKY) ≠ (PCRS − NS in F344 and BN)
Column 6: (PCRS − NS in WKY) ≠ (PCRS − NS in F344, LEW, and BN)
Genes listed above exhibited a change in amygdalar (A) or hippocampal (H) transcript levels according to the same criteria as above.

All publications and patents provided herein incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

I claim:

1. A panel of biomarkers consisting of an isolated set of 100 or fewer full-length cDNA biomarkers, wherein said isolated set includes ALOX15, EIF4G2, and PRDX6 full-length cDNA biomarkers.

2. The panel of biomarkers of claim 1, comprising a full-length TNFRSF1A cDNA biomarker.

3. The panel of biomarkers of claim 1, comprising a full-length NALP12 cDNA biomarker.

4. The panel of biomarkers of claim 1, comprising a full-length CAT cDNA biomarker.

5. The panel of biomarkers of claim 1, comprising a full-length CDR2 cDNA biomarker.

6. The panel of biomarkers of claim 1, comprising a full-length SERPINB1 cDNA biomarker.

7. The panel of biomarkers of claim 1, comprising a full-length LILRB3 cDNA biomarker.

8. The panel of biomarkers of claim 1, comprising a full-length GLRX cDNA biomarker.

9. The panel of biomarkers of claim 1, comprising a full-length IFI27 cDNA biomarker.

10. The panel of biomarkers of claim 1, comprising a full-length FUOM cDNA biomarker.

11. The panel of biomarkers of claim 1, comprising a full-length HSPA8 cDNA biomarker.

12. The panel of biomarkers of claim 1, comprising a full-length IGK cDNA biomarker.

13. The panel of biomarkers of claim 1, comprising a full-length LCMT1 cDNA biomarker.

14. The panel of biomarkers of claim 1, comprising a full-length THYN1 cDNA biomarker.

15. The panel of biomarkers of claim 1, comprising a full-length SEC14L2 cDNA biomarker.

16. The panel of biomarkers of claim 1, comprising a full-length SLC16A3 cDNA biomarker.

17. The panel of biomarkers of claim 1, comprising a full-length SERINC2 cDNA biomarker.

18. The panel of biomarkers of claim 1, comprising a full-length TRPM6 cDNA biomarker.

19. The panel of biomarkers of claim 1, comprising a full-length XKRX cDNA biomarker.

20. The panel of biomarkers of claim 1, comprising a full-length ADN cDNA biomarker.

* * * * *